United States Patent
Vetterlein

(10) Patent No.: US 6,626,047 B1
(45) Date of Patent: Sep. 30, 2003

(54) CRACK TESTING ARRANGEMENT WHICH IS ESPECIALLY USED AFTER THE DYE-PENETRATION METHOD OR MAGNETIC METHOD

(76) Inventor: Thomas Vetterlein, Hofherrnstrasse 67 a, 73434 Aalen (DE)

(*) Notice: Subject to any disclaimer, the term of this patent is extended or adjusted under 35 U.S.C. 154(b) by 0 days.

(21) Appl. No.: 09/647,315

(22) PCT Filed: Feb. 4, 2000

(86) PCT No.: PCT/DE00/00352

§ 371 (c)(1), (2), (4) Date: Sep. 28, 2000

(87) PCT Pub. No.: WO00/47982

PCT Pub. Date: Aug. 17, 2000

(30) Foreign Application Priority Data

Feb. 8, 1999 (DE) .................... 299 02 218 U

(51) Int. Cl.⁷ .............................. G01L 1/24
(52) U.S. Cl. ............................ 73/800; 73/794
(58) Field of Search .................. 73/799, 800

(56) References Cited

U.S. PATENT DOCUMENTS

| | | | | |
|---|---|---|---|---|
| 3,748,469 A | * | 7/1973 | Molina | 250/459 |
| 4,836,031 A | * | 6/1989 | Jatho et al. | 73/800 |
| 4,856,326 A | * | 8/1989 | Tsukamoto | 73/150 A |
| 5,003,831 A | * | 4/1991 | Link et al. | 73/104 |
| 5,020,908 A | * | 6/1991 | Hermann | 356/239 |
| 5,115,136 A | | 5/1992 | Tomasch | |
| 5,374,821 A | * | 12/1994 | Muhs et al. | 73/800 |
| 5,554,318 A | | 9/1996 | Neumann et al. | |

FOREIGN PATENT DOCUMENTS

| | | |
|---|---|---|
| DE | 2417232 | 11/1975 |
| EP | 0831321 | 3/1998 |

* cited by examiner

Primary Examiner—Max Noori
(74) Attorney, Agent, or Firm—Bachman & LaPointe, P.C.

(57) ABSTRACT

The invention relates to a crack testing system using the dye penetration method or for magnetic crack testing, having an illumination unit, a device for applying testing material and an evaluation station, which has light-emitting diodes (LEDs) as illumination units.

4 Claims, 3 Drawing Sheets

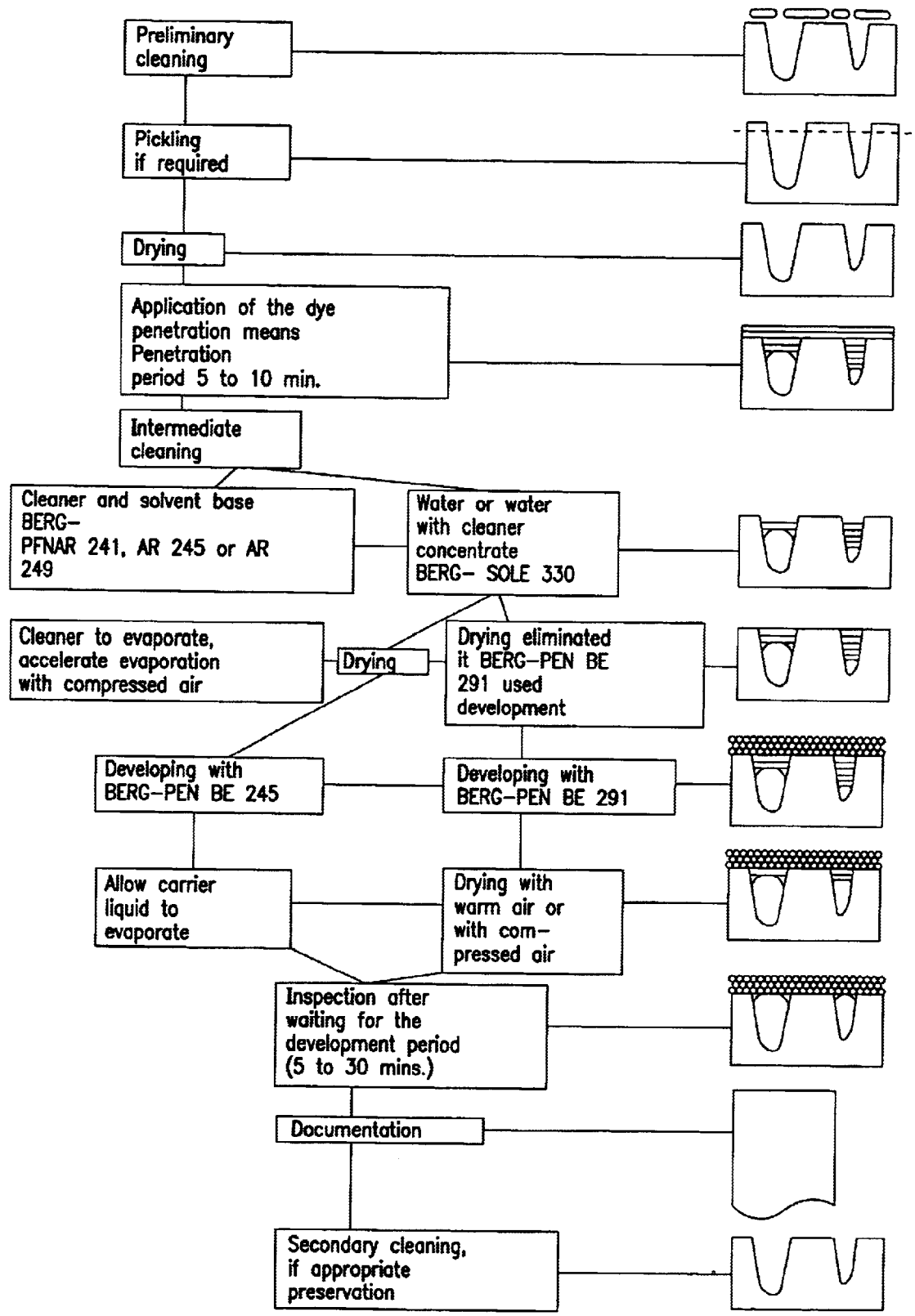
FIG. IA

CRACK TESTING ARRANGEMENT WHICH IS ESPECIALLY USED AFTER THE DYE-PENETRATION METHOD OR MAGNETIC METHOD

Crack testing system, in particular using the dye penetration method or magnetic method.

The invention relates to a crack testing system using the dye penetration method or for magnetic crack testing, having an illumination unit, a device for applying testing material and an evaluation station.

Various crack testing methods are known in the prior art—generally, for magnetizeable test pieces, in particular those made from iron, use is made of a magnetic powder method in the case of which magnetic dye particles accumulate at cracks and the like in a magnetic field at the test piece and are then detected under illumination. The dye is frequently fluorescing, and the contrast is thereby improved.

For non-magnetizeable materials, it is customary to use a so-called "black powder method"—use is made of dye solutions which accumulate in the cracks because of surface phenomena and capillary phenomena and can then be detected there within the specific test period. Such methods are known, for example, from EP 0831 321.

In both methods, use has been made for illumination purposes of conventional lamps—such as mercury vapor lamps, gas discharge lamps, flashlamps and this, in particular, because fluorescing dyes, which are used with particular alacrity, are most excited in the UV or in the blue range of the visible spectrum. Conventional lamps, in particular—those having thermal emitters, undergo severe aging. Even after a few burning hours, the UV component of such lamps is greatly reduced. Since, in particular, the UV component of the lamps is required for the fluorescence excitation, in the case of the known crack testing systems the lamp power must be expensively monitored and readjusted. Continuously changing intensities of the illuminating light can cause substantial false displays in the currently customary optical detection methods via image processing, for which reason lamp monitoring is expensive. Thus, for example, a system for lamp checking in crack testing systems of the generic type has become known from DE-A-40 13 133.5.

It is therefore the object of the invention to create a crack testing system with lamp monitoring which is less expensive.

This object is achieved according to the invention by means of a crack testing system which has light-emitting diodes (LEDs) as illumination units.

Advantageous developments follow from the subclaims.

According to the invention, the following advantages, inter alia, are achieved thereby: LEDs are not subject to aging phenomena—that is to say, the intensity of the emitted light remains constant and the emission spectrum is not subject to drift—that is to say, the previously required expensive lamp monitoring and readjustment of the same can be eliminated, and a substantial simplification of the system is achieved.

LEDs are of small size and can also be installed at inaccessible sites.

LEDs radiate little warmth, as a result of which it is possible eliminate cooling measures, or else precautionary measures which have been required in the case of lamps in order to avoid burning.

Because of their emission, LEDs can excite a dye for fluorescence/phosphorescence at specific absorption wavelengths, as a result of which in the event of the use of various dyes the latter can be excited individually—for example if part numbers have been applied with a specific dye, the dye of the crack testing material has a different fluorescence wavelength and both are to be detected by the optical detection system for the purpose of individualizing the parts to be tested.

LEDs can easily be optically coupled to optical conductors, which can easily be led to inaccessible sites.

It is advantageous to use LEDs which emit in the region from 200 to 970 nm, since the dyes to be used absorb here.

It is favorable that the LED voltage can be modulated, since an improved signal processing by a processor is possible thereby.

LEDs can be optically coupled to optical conductors which conduct the illuminating light in the system.

In a specific embodiment of the invention, it is also possible to make use of a light distributor which splits light from a light source and thus permits the use of only one light source for different light outlets, as a result of which it is possible to eliminate controlling a plurality of lamps, their maintenance etc., or to limit controlling to only a single light source.

It can be favorable that if the crack testing system has a processor for controlling the devices for optical image processing, said processor also controls the LED power supply.

The invention is explained in more detail with the aid of a preferred exemplary embodiment, to which it is not, however, limited in any way, and with the aid of the enclosed drawing, in which:

FIG. 1a shows a schematic of the sequence of a crack testing method;

FIG. 1b shows a first embodiment of a crack testing system according to the invention for carrying out the method according to FIG. 1a.

FIRST EXEMPLARY EMBODIMENT—CRACK TESTING SYSTEM USING THE DYE PENETRATION METHOD

As shown in FIG. 1a, in the case of crack testing methods using the dye penetration method in most cases a non-ferritic test piece—e.g. an aluminum or magnesium piece, or else a ceramic piece is cleaned, pickled if appropriate and dried and then treated with the testing material—also designated as dye penetration means. The excess dye penetration means are removed after a specific period, the workpiece is subjected to intermediate cleaning and then treated with a developing solution. After the developing time, the workpiece is, if appropriate, dried and inspected, and a statement is made on the defectiveness of the workpiece which is also documented, if appropriate.

Figure 1B:
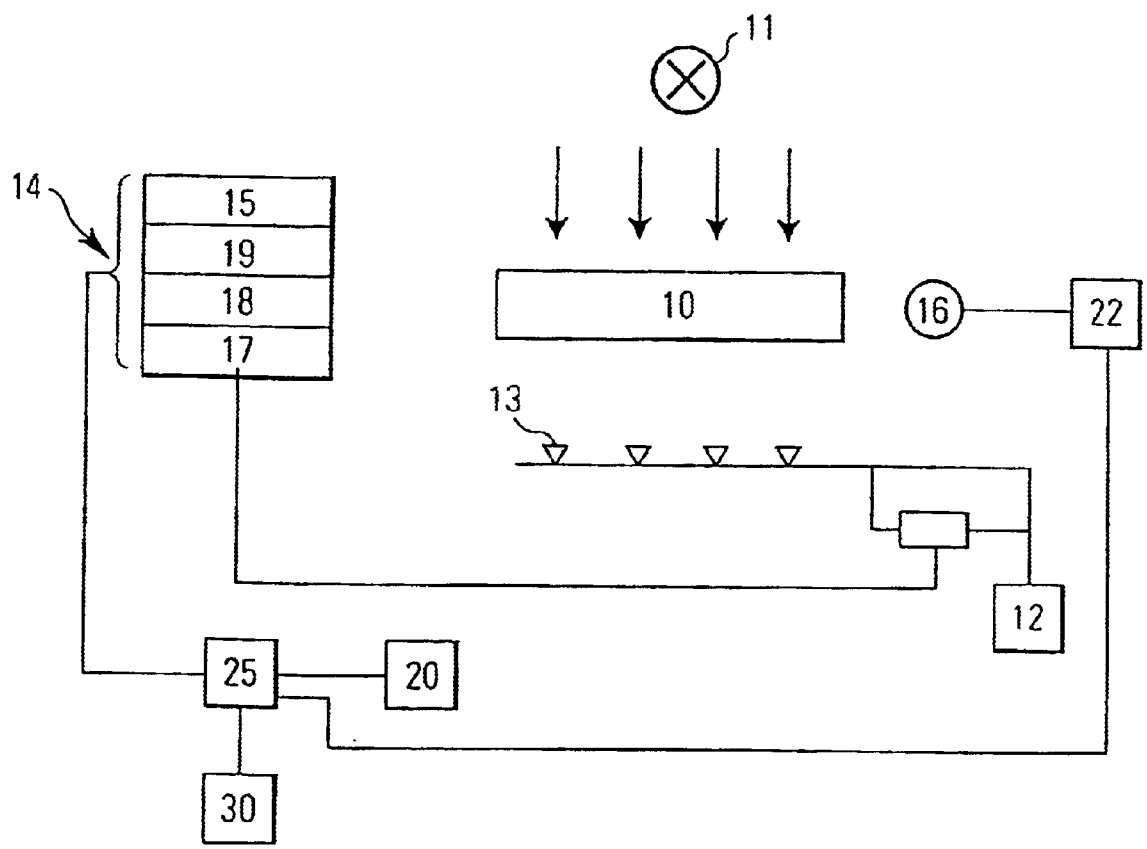

As shown in FIG. 1b, in this case a developed workpiece 10 is guided as test piece into a testing station in which the dye penetrating means is applied from a tank 12 of dye penetrating means by spray nozzles 13—this is illustrated only by way of example—in fact, the test piece traverses a plurality of stations in which it is treated with cleaning and pickling solutions and also developing solutions and dyeing solutions, which are not illustrated here.

There, the testing material is checked for functionality, and dye or the like can, if appropriate, be metered subsequently into the tank 12 if this is necessary.

Testing liquid 13a which serves to mark the surface defects is fed from a storage container 12 via a feed line by means of spray heads 13 and atomized above the surface of the workpiece 10. The testing liquid is now distributed on the workpiece, the dye particles concentrating at cracks by virtue of the surface tension—as is generally known as a physical phenomenon. There is then an increased particle concentration at these sites. The excess testing liquid is removed, for example, by being wiped away. Consequently, the test piece is processed using a developing liquid. After expiry of a developing time to be determined experimentally for each test arrangement and test piece—a lamp—here an LED 11 is used to irradiate the surface of the workpiece 10, the contrast of the testing liquid particles is thereby raised, and the dye particles accumulating in the region of the surface cracks are observed and/or their inhomogeneous arrangement is evaluated. For the sake of the functional reliability of the system, it is possible to provide a self-checking device for the monitoring or self-monitoring of associated operating parameters, that is to say the observance of the respective operating parameters within the prescribed value intervals which, whenever the measured values are outside a desired range of measured values, can make any adjustments within specific limits, as a result of which it is possible to avoid unnecessary waste of material such as occurs through premature replacement of the marking means. The service life of the testing system is substantially lengthened thereby, the system can run longer without interruptions, and the operating costs associated therewith, as well as the costs of material and energy are likewise lowered as a consequence thereof. The self-checking device is connected here to a documentation device, a printer, in which it draws up test records with the aid of which the functionality of the system can be demonstrated. of course, the documentation device is not limited to printers—instead of this, optical data media, such as CD ROMS, can be used, or else storage on other magneto optic media is possible, as described in EP-A-0 831 321.

The actual detection and outputting of the measured values of the measuring units, as individually known per se, can be performed as follows: the monitoring of the functionality of the measuring unit 14 can additionally still be carried out with the aid of a test body which has a test crack, as described in DE-A-3804054. Preferably, the automatic measuring unit 17 for the testing material is an automated "ASTM bulb, as described in EP-A-0788 598.

SECOND EXEMPLARY EMBODIMENT—CRACK TESTING SYSTEM USING THE MAGNETIC POWDER METHOD

In an automatic defect-detecting system for crack testing for in-process monitoring via imaging processing using the magnetic powder method, regions of higher concentration of magnetizeable particles which can fluoresce are determined on workpieces, said regions being caused to fluoresce by fluorescence-exciting LEDs; these, being one or more recording units; a testing material application system and an image processing unit, which is suitable for evaluating image units, recorded with the aid of the recording units, by scanning and detecting brighter regions, and for outputting various signals on the basis of the evaluation logic.

Automated optical defect detection in magnetic powder testing in production systems which continuously manufacture workpieces to be checked such as, for example, continuous casting installations, wire-end testing systems or the like is known. Images of workpieces with the aid of fluorescent dyes are already being evaluated by means of so-called optical image detection, the defects rendered visible by means of the magnetic powder method, which is known per se, being detected by an optical scanning and image detection method and being compared with the aid of a stored defect logic.

In test pieces with edges, boreholes, etc., testing material is deposited on edges. This means that, compared with using the eye to evaluate displays, testing with the aid of the camera is possible only by forming windows. Consequently, the "holistic observation" of the test piece which humans can conduct is lost, and normally only the safety-relevant part is assessed by windows. A very exact positioning of a test piece in front of the camera is required in order to minimize the surfaces not tested by the testing windows set. A frequent result of manufacturing tolerances and positioning tolerances in the case of test samples is that only approximately 80–85% of the safety-relevant test area can be tested.

Evaluating the crack defect display with the aid of cameras does not solve problems relating to the assignment of crack geometry to the intensity of the display and to the bead size. The camera distinguishes only differences in brightness, and therefore all parameters which influence the brightness have to be included in the reproducibility of the crack defect.

The recording units can advantageously be cameras, preferably video cameras. However, it is also possible to use other detection devices such as, for example, diode arrays, photomultiplier arrangements etc.

The optical image processing is preferably performed in the system by setting windows, scanning the windows by means of the image evaluation unit and processing the data thereby obtained in a computer.

It is possible in this case for the system to be halted/cut down by the signals of the computer.

Figure 2:
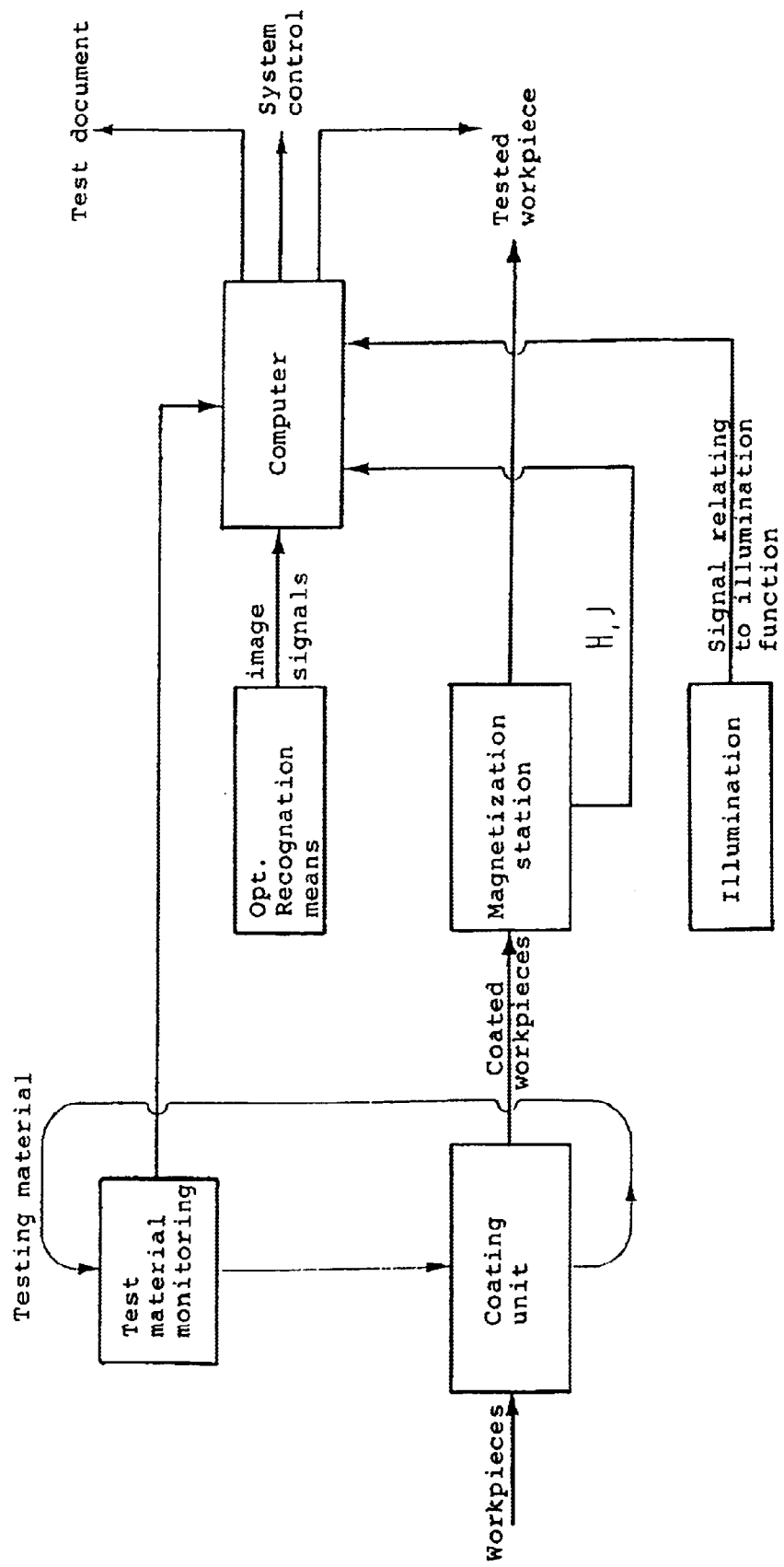
FIG. 2 shows a second embodiment of a crack testing system according to the invention for the magnetic powder method.

As may be seen from FIG. 2, in the automatic crack testing method workpieces are first treated with crack testing material in a coating unit is (immersion or spray unit, with ultrasonic treatment if appropriate). Crack testing material is usually a suspension of a magnetizeable or preferably ferromagnetic particulate material which can fluoresce and in which the workpiece is immersed or which is sprayed on to the workpiece.

After application of the crack testing material, current is applied to the workpiece, thereby producing a magnetic field in which the ferromagnetic particles are aligned. On the basis of known physical phenomena, increased particle concentrations are found in this case at tips and edges and result in the particles accumulating not only at the edges of the workpiece but also at crack edges or tips/burrs of defects in the workpiece, which also act as edges. The parts thus coated are then irradiated by means of an LED, the regions of increased particle concentration emitting more brightly by fluorescence than the normal metal surfaces.

The fluorescence images are taken by means of an optical recognition means—either scanned according to a predetermined pattern, or taken as a whole, and the image is subsequently evaluated. The result of this image recording is then led to a computer which compares this recording with stored values and uses a program to output information on the workpiece which can lead to assessment of the workpiece. According to the invention, the computer now also receives data from the checking system itself, specifically from a testing material monitoring system on the functionality of the testing material, from an illumination checking unit on the functioning of the illumination, for example LED; from the magnetization station on the conductive continuity and on the magnetic field built up by the workpiece; from the optical recognition means on the functioning thereof (if appropriate, focus, distance from the measurement object, functionality of the camera). These signals can be processed individually or jointly to produce a record which can be output, if appropriate, as a test record on a printer or another medium, such as paper. The functioning of the system at specific times can be documented at any time by means of this test record.

The signals produced by the computer can be sent to a workpiece feeder in order to halt the workpiece feeding or to shut down the system. It is also possible for these signals to be used specifically for readjusting system parameters such as, for example, setting the focus of the recording units, or the geometrical arrangement of the same; for supplying new crack testing material if the old one has been used up, readjusting the current flowing through the workpiece; etc.

By virtue of the fact that the crack testing system itself is now being monitored for the first time, said system operates more reliably and more precisely than previously, and the reproducibility of the measured values is ensured.

The system can also be continuously monitored (simultaneously, if appropriate) using monitoring data which are output on monitors and can be monitored by an operator who can then take measures.

In this case, different monitoring parameters are determined and transmitted to the computer.

Thus, the invention permits generic systems to be simplified and improved, as a result of which it is possible to improve the system performance without complicated external control of the power supply of the lamps, expensive electronic monitoring with lamp sensors, and also to reduce dimensions of the system.

Although the invention has been explained with the aid of preferred exemplary embodiments, it is in no way limited to these, but also relates to the modifications familiar to the person skilled in the art as they are defined by the scope of the claims.

What is claimed is:

1. An apparatus for detecting cracks on non-transparent objects comprises:

means for applying a dye which absorbs light in the region from 200 to 970 nm on non-transparent object wherein the dye accumulates in any cracks; and means for detecting accumulated dye in the cracks, said means for detecting comprises light emitting diodes ($LED_s$) which emit light in the region from 200 to 970 nm.

2. The apparatus as claimed in claim 1, wherein said means for detecting further includes means to modulate the $LED_s$ voltage.

3. The apparatus as claimed in claim 1, including means for optically coupling the $LED_s$ to optical conductors for conducting light.

4. The apparatus as claimed in claim 1, including a processor for controlling (1) a device for optical image processing and (2) a LEDs power supply.

* * * * *